United States Patent [19]
Kroll

[11] Patent Number: 5,383,907
[45] Date of Patent: Jan. 24, 1995

[54] SYSTEM AND METHOD FOR DELIVERING MULTIPLE CLOSELY SPACED DEFIBRILLATION PULSES

[75] Inventor: Mark W. Kroll, Minnetonka, Minn.

[73] Assignee: Angeion Corporation, Plymouth, Minn.

[21] Appl. No.: 993,292

[22] Filed: Dec. 18, 1992

[51] Int. Cl.6 ............................................. A61N 1/36
[52] U.S. Cl. ....................................................... 607/5
[58] Field of Search ..................... 607/5; 320/1, 9, 20, 320/3; 307/106, 108, 109, 110, 150, 154; 315/160, 175

[56] References Cited

U.S. PATENT DOCUMENTS

| | | | |
|---|---|---|---|
| 3,211,154 | 10/1965 | Becker et al. | 607/5 |
| 4,025,860 | 5/1977 | Shibata et al. | 320/3 |
| 4,530,550 | 7/1985 | Kondo | 320/1 |
| 4,637,397 | 1/1987 | Jones et al. | 607/5 |
| 4,931,947 | 6/1990 | Werth et al. | 320/3 |

Primary Examiner—Lee S. Cohen
Assistant Examiner—Marianne Parker
Attorney, Agent, or Firm—Patterson & Keough

[57] ABSTRACT

A main energy delivery electrical circuit for use in an implantable cardioverter defibrillator device comprises a low power output primary defibrillator battery, a high power output intermediate power intensifying battery, a switch for permitting the intermediate power intensifying battery to rapidly charge a main energy delivery capacitor, and a main energy delivery capacitor. The main energy delivery capacitor is configured for discharging, in a first pulse, an electrical charge derived from the primary battery and for discharging certain subsequent pulses of electrical charge derived from the intermediate power intensifying battery. The circuit permits the implantable cardioverter defibrillator device to deliver multiple closely spaced defibrillation pulses to a heart.

27 Claims, 3 Drawing Sheets

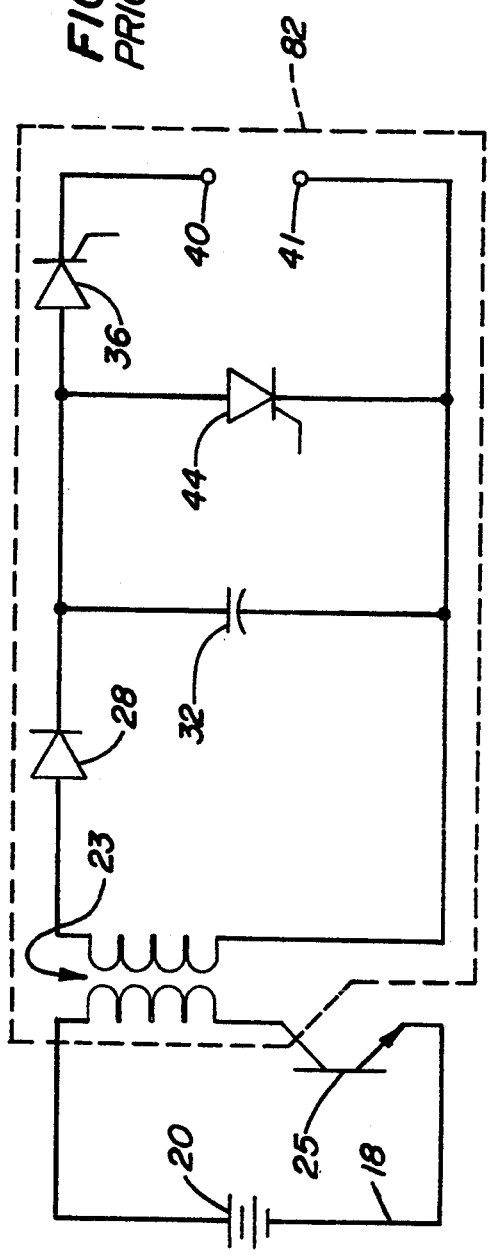
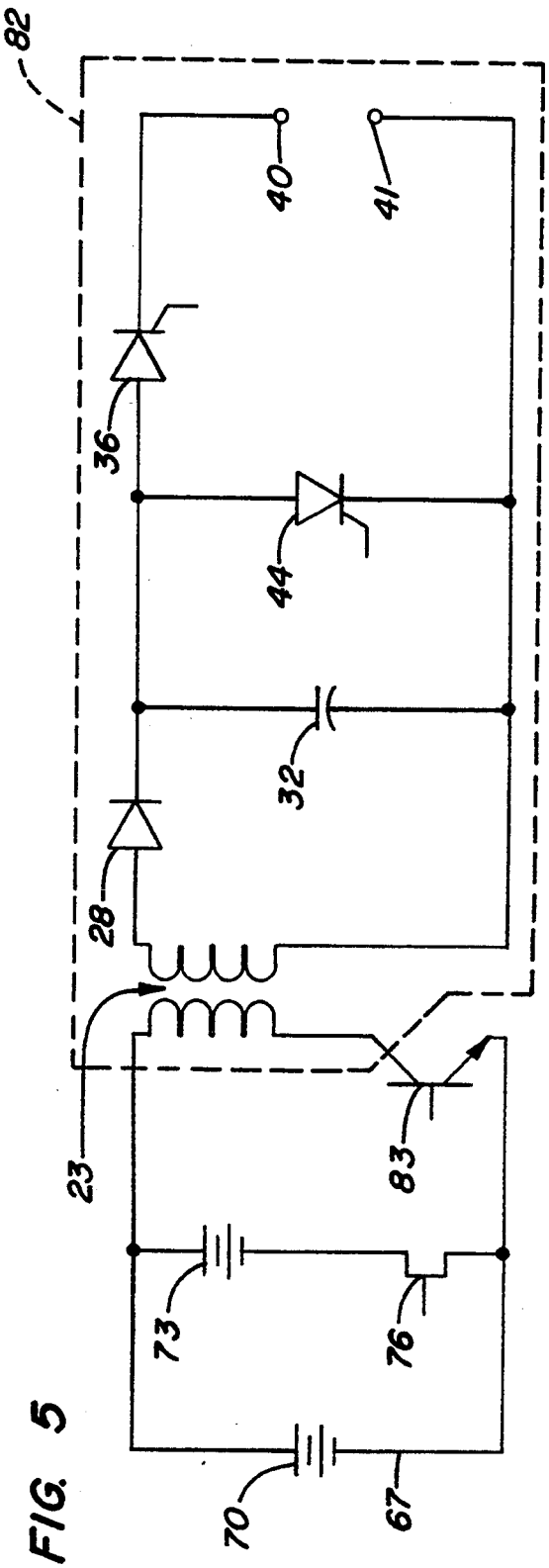
FIG. 2 PRIOR ART
FIG. 5

SYSTEM AND METHOD FOR DELIVERING MULTIPLE CLOSELY SPACED DEFIBRILLATION PULSES

FIELD OF THE INVENTION

A system and method is disclosed for delivering closely spaced multiple defibrillation pulses. More particularly, the amount of energy required in each pulse is low, which reduces the overall size of the capacitor required for pulse delivery. This also reduces the overall size of an implantable cardioverter defibrillator device utilizing the capacitor.

BACKGROUND OF THE INVENTION

Electrical defibrillation of the heart has been accomplished in a research and clinical setting for many years. Recently, implantable cardioverter defibrillators, known as ICDs, have been used to provide defibrillation pulses in these settings. The pulses may vary between monophasic and biphasic pulses. A multiple pulse technique was also developed for defibrillation which comprises a plurality of shorter duration pulses, possibly with a variety of spacing between the pulses. In all of the above methods, a minimum energy requirement exists which requires storage capacitors of certain size. Optimization of capacitor size, in combination with the advantages of the theoretically optimum multiple pulse technique is desirable.

Efforts to create improved power generation and distribution systems in multiple pulse defibrillation devices are demonstrated in many U.S. patents. However, considerable advances are necessary to reduce the level of intrusion which ICD devices create in the patient and to optimize the performance of the devices.

SUMMARY OF THE INVENTION

A main energy delivery electrical circuit for use in an implantable cardioverter defibrillator device comprises a low power output primary defibrillator battery, a high power output intermediate power intensifying battery, a switch for permitting the intermediate power intensifying battery to rapidly charge a main energy delivery capacitor, and a main energy delivery capacitor. The main energy delivery capacitor is configured for discharging, in a first pulse, an electrical charge derived from the primary battery and for discharging certain subsequent pulses of electrical charge derived from the intermediate power intensifying battery. The circuit permits the implantable cardioverter defibrillator device to deliver multiple closely spaced defibrillation pulses to a heart.

A main energy delivery electrical circuit for use in an implantable cardioverter defibrillator comprises a low power output primary defibrillator battery, a high power output intermediate power intensifying battery, a main energy delivery capacitor, and a charging sub-circuit. The main energy delivery capacitor is configured for discharging, in a first pulse, an electrical charge derived from the primary battery and for discharging certain subsequent pulses of electrical charge derived from the intermediate power intensifying battery. The charging sub-circuit permits simultaneous charging from the low power output primary defibrillation battery to both the high power output intermediate power intensifying battery and the main energy delivery capacitor.

A rapid pulse power system for use with an implantable cardioverter defibrillator is provided. The system permits rapid transition from a widely spaced defibrillation pulse sequence to a closely spaced defibrillation pulse sequence. The rapid pulse power system comprises a low power output primary defibrillator battery, a high power output intermediate power intensifying battery, switch means for permitting the intermediate power intensifying battery to rapidly charge a main energy delivery capacitor, control means for responding to a remote signal and selectively discharging a main energy delivery capacitor, and a main energy delivery capacitor. The capacitor is configured for discharging, in a first pulse, an electrical charge derived from the primary battery and for discharging certain subsequent pulses of electrical current derived from the intermediate power intensifying battery. The circuit permits the implantable cardioverter defibrillator device to deliver multiple closely spaced defibrillation pulses to a heart at any time interval following an initial defibrillation attempt.

BRIEF DESCRIPTION OF THE DRAWINGS

FIG. 2 is a schematic circuit diagram illustrating representative prior art circuitry for an implantable cardioverter defibrillator.

FIG. 5 is a schematic circuit diagram of one embodiment of the implantable cardioverter defibrillator rapid pulse circuitry of this invention.

DETAILED DESCRIPTION OF THE INVENTION

Figure 1:
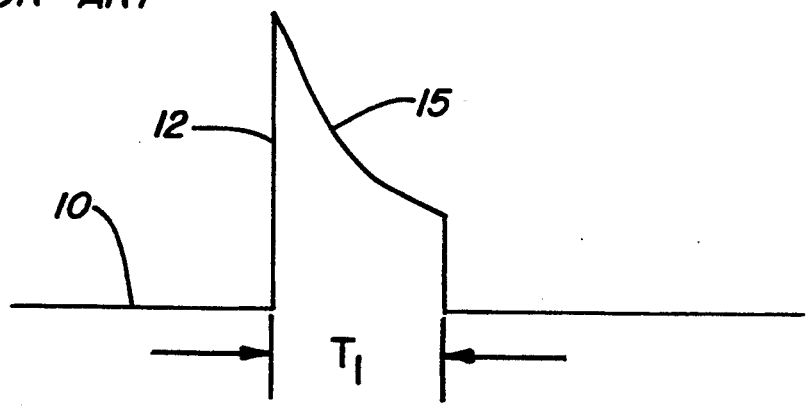
FIG. 1 is a representative monophasic waveform for an implantable cardioverter defibrillator.

FIG. 1 illustrates a common waveform utilized by implantable cardioverter defibrillators. Waveform 10 discloses the monophasic pulse portion 12 exhibited during capacitive discharge. Monophasic pulse 12 is derived by charging a large capacitor to high voltage and discharging that capacitor into the heart. After a period of time $T_1$ has elapsed, the current flow is removed which results in the truncated shape 15 of the monophasic pulse 12.

FIG. 2 illustrates representative circuitry for generating a pulse similar to that disclosed in FIG. 1. Circuit 18 comprises battery 20 which is used to provide a current through the primary winding of transformer 23. The current is cycled on and off at a high rate of speed by switching transistor 25. The output from transformer 23 is rectified by diode 28 and is captured in the main storage capacitor 32. In order to deliver the pulse to the heart, silicon controlled rectifier 36 is triggered providing a current path from capacitor 23 to the electrodes 40, 41 in the heart. At the point of pulse truncation at the end of time period $T_1$, silicon controlled rectifier 44 is triggered. This quickly discharges capacitor 32 and back biases silicon controlled rectifier 36 to shut off the flow of current through electrodes 40, 41 to the heart.

Figure 3:
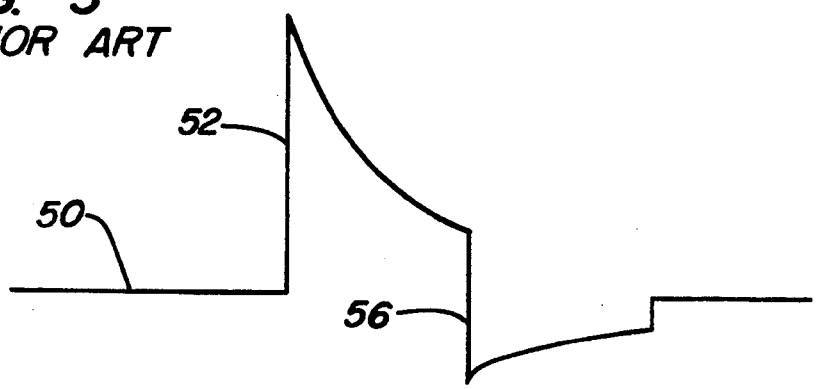
FIG. 3 is a representative biphasic waveform for an implantable cardioverter defibrillator.

The biphasic waveform 50 depicted in FIG. 3 is an improvement over the monophasic waveform 10 of FIG. 1. Biphasic pulse 52 commences with a first phase that is substantially identical to that of monophasic pulse 12. However, at the time of truncation following time period $T_1$ the current is not merely interrupted but is reversed, producing the configuration shown as pulse section 56. This reversal is commonly done by the use of current reversal means, such as H-bridge circuitry, not shown here. Use of a biphasic pulse technique may reduce the energy required for each defibrillation pulse by about an average of 25 percent.

The energy required to defibrillate in each pulse is a critical determinant of the size of an implantable cardioverter defibrillator. This is because the main storage capacitor, such as capacitor 32 shown in FIG. 1, is normally the largest single component in such an ICD device. The most efficient proven capacitors of this type will store about 1.5 Joules per cubic centimeter, and are also the major determinant of the volume of an implantable cardioverter defibrillator. Since this class of defibrillator device is implantable, it is critical that it be made as small as possible. This is particularly important as now ICD devices are designed for pectoral implantation. This directly translates into a severe constraint on the volume of the device and the energy available per defibrillation pulse.

Figure 4:
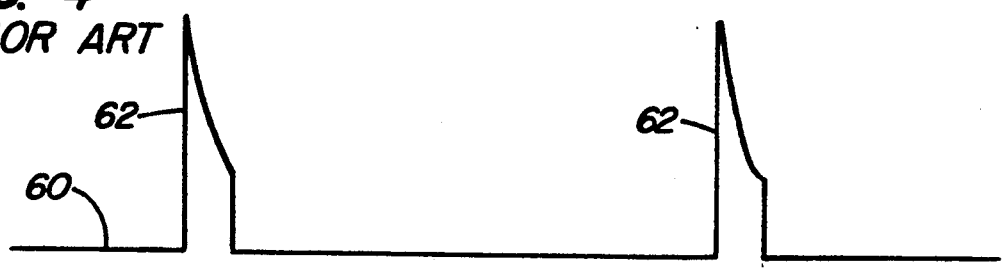
FIG. 4 is a conceptual multiple short pulse waveform for a defibrillator.

The multiple pulse defibrillation concept as generally shown in FIG. 4 has been experimented with for many years. Ventricular defibrillation of dogs with waves comprising two pulses with a pulse length and pulse interval adjusted so that those cells excitable at any moment are defibrillated by the first pulse and are refractory to the second pulse was disclosed by Kugelberg as early as October 1965, in the Scandinavian Society of Thoracic Surgery, pages 123-128. Kugelberg considered a variety of pulses and spacings and found that defibrillation was indeed quite possible with multiple pulses. U.S. Pat. No. 4,996,984, issued to Sweeney, discloses adjusting the timing between multiple bursts of defibrillation energy based upon the fibrillation cycle length of the mammal. Similarly, Sweeney and Reid disclose that the interaction between multiple pulses is non-linearly related to the fibrillation cycle length, and that the spacing between multiple pulses may be a fixed percentage of the spacing between fibrillation zero crossings in the heart. (II-610, Supplement II Circulation, Vol. 84, No. 4, October 1991, No. 2425). Johnson et al disclose that successive biphasic shocks delivered through two different electrodes may be either beneficial or detrimental depending on the delay between the two shocks. (NASPE Abstracts, April 1991, Part II, no. 391; PACE, Vol. 14, p. 715). Other examples of multiple pulse defibrillation systems include U.S. Pat. Nos. 5,107,834 to Ideker et al and 4,708,145 to Tacker, Jr. et al.

In principal, the above disclosures demonstrate that the energy per pulse in a multiple or closely spaced pulse technique using different pathways, multiple defibrillators, or other inefficient means of energy generation and distribution, may be reduced from what is commonly used in a single or widely spaced pulse technique. These are considerable limitations and disadvantages in the field of implantable cardioverter defibrillators.

Current medically accepted practice requires a minimum amount of energy for implantable cardioverter defibrillators on the order of about 20-30 Joules. The multiple pulse waveform 60 of FIG. 4 depicts activation of a representative multiple defibrillator system. The system would likely lower the total defibrillation threshold by about 50 percent, cutting the 30 Joule accepted limit to about 15 Joules per pulse. However, such a system requires multiple sizeable capacitors. No disclosure exists for either a method or structure to achieve multiple closely spaced pulses using an intermediate power intensifier as disclosed below. The present invention teaches means for overcoming the impediments of the theoretical multiple pulse systems. The invention also discloses novel means for providing a rapid pulse power system for use with conventional ICD circuits to permit optional prompt transition from a widely spaced defibrillation pulse sequence to a closely spaced defibrillation pulse sequence.

The energy generation problem is appreciated more fully by calculating the charging power required of a representative capacitor system in an ICD device. Assuming a conventional single pulse defibrillator which is designed to deliver a 30 Joule pulse, a 10 second delay for capacitor charging is considered acceptable after fibrillation is detected. The charging power is described by simple calculation of 30 Joules divided by 10 seconds, which yields 3 watts. This 3 watt level of power is available from high quality defibrillation primary cells, such as lithium silver vanadium pentoxide cells, although others may be suitable.

Assuming a use of two closely spaced pulses 62, 63, as shown in waveform 60 of FIG. 4, defibrillation could occur with 15 Joules in each pulse. The capacitor could be designed to store only 15 Joules and could be made of only half the size of present capacitors. However, although the capacitor has 10 seconds to charge in order to create the first pulse 62 by use of present circuitry, the capacitor then must be quickly recharged to provide the second pulse 63. Generally, the amount of time required to quickly recharge is the same time as that required for optimum spacing between the two pulses, which is about 0.25 seconds. Therefore, the charging power must be equal to 15 Joules divided by 0.25 seconds. This requires a 60 watt power source. Currently, there is no functional implantable battery which is capable of providing such power output.

FIG. 5 discloses the essential circuit elements of one embodiment of the present invention in which circuit 67 uses both a primary battery and an intermediate power intensifying battery, with the latter comprising a very high power output battery to provide the high charging power between capacitor pulses. As shown, battery 70 is a low amperage primary defibrillation cell, which is preferably a lithium silver vanadium pentoxide type, although other materials are feasible. When fibrillation is detected, battery 70 is used to quickly charge a rechargeable battery 73 which is capable of very high power output. This is preferably accomplished through the use of transistor switch 76. Battery 73 is preferably selected from a list of possible high power rechargeable batteries, such as a lithium titanium disulfide, lithium sulphur dioxide, or others suitable for producing the desired power in a rechargeable configuration. When battery 73 has been sufficiently charged then it is useful as a source of high current charging power to capacitor 32 in circuitry sub-section 82, shown in circuit 18 of FIG. 2 and in circuit 67 of FIG. 5.

The difference between the capacitor charging circuitry of FIG. 5 and FIG. 2 is an approximately 20:1 charging power ratio of 60 watts rather than 3 watts. The charging circuitry shown as schematic circuit 67 provides power means for recharging the capacitor of the related ICD device, after an initial discharge, between subsequent multiple pulses. This eliminates additional capacitors and eliminates about half of the capacitor volume of known ICD devices. The invention also results in significant improvement in size and operation of an ICD device.

An alternate embodiment for charging rechargeable battery 73 after fibrillation is detected comprises maintaining battery 73 substantially charged at all times. This may be accomplished by a variety of methods, including using primary battery 70 to provide a continuous nominal charge to battery 73, which is a recharging technique similar to that disclosed in co-pending U.S. patent application Ser. No. 07/993,094, filed concurrently on Dec. 18, 1992, and titled Staged Energy Concentration for a Defibrillator.

Figure 6:
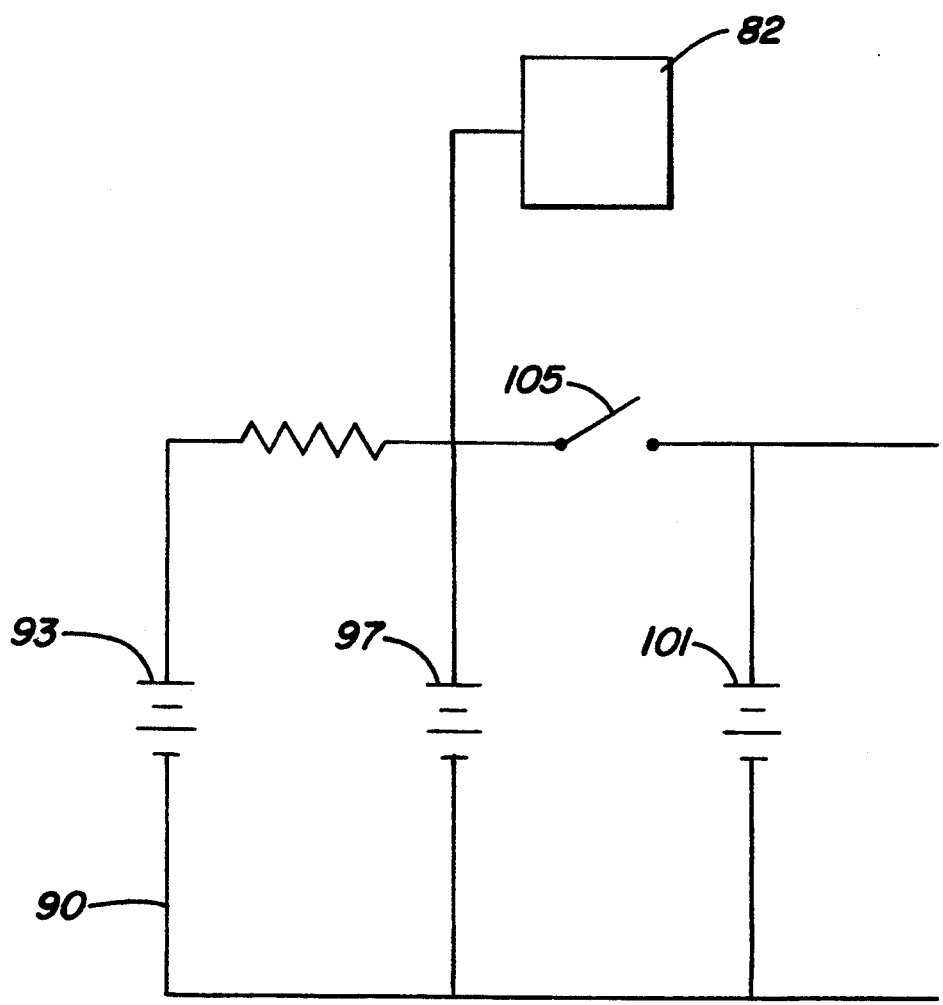
FIG. 6 is a schematic circuit diagram of another embodiment of the implantable cardioverter defibrillator rapid pulse circuitry of this invention.

Another alternate embodiment for charging rechargeable battery 73 after fibrillation is detected is disclosed in FIG. 6. In this embodiment, circuit 90 comprises a relatively low amperage, e.g. milliamps, primary defibrillation battery 93. One example of such a battery 93 comprises a pacing type lithium iodide battery, although other materials are also suitable. Circuit 90 also comprises high power output (approximately 1-3 amps) intermediate power intensifying battery 97. A preferred battery 97 comprises a lithium titanium di-sulfide battery. Battery 101 comprises a very high amperage (10–30 amps) battery. In operation, circuit 90 allows continuous trickle charge from battery 93 to battery 97. This maintains battery 97 in a substantially fully charged configuration until detection of fibrillation. After detection of fibrillation, battery 97 simultaneously charges the main energy delivery capacitor 32 within sub-section 82 and battery 101, via switch 105. Capacitor 32 then discharges and is again re-charged with battery 97. However, battery 97 is not normally able to fully charge capacitor 32 in less than at least about 5 seconds. In a closely spaced multiple pulse ICD device power system it is necessary to provide means other than battery 97 to provide charging power for subsequent pulses to the heart. Rather than providing multiple charging pathways or a plurality of capacitors, circuit 90 discloses use of battery 101 to provide high amperage high power means for charging a main energy delivery capacitor for countershock pulses after the initial countershock/pulse.

The invention also comprises a method for configuring an implantable cardioverter defibrillator main energy delivery electrical circuit for delivery of multiple closely spaced defibrillation pulses to a heart. The method comprises the steps of providing a low power output primary defibrillator battery, and arranging a high power output intermediate power intensifying battery with switch means for permitting the intermediate power intensifying battery to be rechargeable from the primary defibrillator battery and to selectively rapidly charge a main energy delivery capacitor. A main energy delivery capacitor is electrically configured for discharging, in a first pulse, electrical current derived from the primary defibrillator battery and for discharging certain subsequent pulses of electrical current derived from the intermediate power intensifying battery so that the circuit permits the implantable cardioverter defibrillator device to deliver multiple closely spaced defibrillation pulses to a heart using a single capacitor. A further step comprises simultaneously charging both the high power output intermediate power intensifying battery and the main energy delivery capacitor using the low power output primary defibrillator battery.

The embodiment of circuits 67 and 90 are each also advantageous as a rapid pulse power system for use with implantable cardioverter devices. This rapid pulse power system may be integrated into other known or proprietary circuits as a means of enabling rapid and optional transition from a widely spaced defibrillation pulse sequence to a closely spaced defibrillation pulse sequence. This is accomplished without adding any additional capacitors, which would detract from the size and volume advantages of the invention. Accordingly, the invention also discloses a method of configuring an implantable cardioverter defibrillator electrical circuit as a rapid pulse power system to enable rapid transition from a widely spaced defibrillation pulse sequence to a closely spaced defibrillation pulse sequence. The method comprises the steps of providing a low power output primary defibrillator battery, arranging a high power output intermediate power intensifying battery, providing switch means for permitting the intermediate power intensifying battery to rapidly charge a main energy delivery capacitor, responding to a remote signal and selectively discharging a main energy delivery capacitor. The main energy delivery capacitor is discharged, in a first pulse, with an electrical charge derived from the primary defibrillator battery and, in certain subsequent multiple closely spaced defibrillation pulses, with electrical charge derived from the intermediate power intensifying battery. The pulses are deliverable to a heart at any time interval following an initial defibrillation attempt using another defibrillator pulse power source.

I claim:

1. A main energy delivery electrical circuit for use in an implantable cardioverter defibrillator device, comprising:
   a) a low power output primary defibrillator battery;
   b) a high power output intermediate power intensifying battery;
   c) switch means, electrically connected to the intermediate power intensifying battery and the low power output primary defibrillator battery, for selectively switching between the primary defibrillator battery and the intensifying battery; and
   d) a main energy delivery capacitor connected to the switch means for discharging, in a first pulse, an electrical charge from the primary battery and for discharging one or more subsequent pulses of electrical charge derived from the intermediate power intensifying battery so that the electrical circuit permits the implantable cardioverter defibrillator device to deliver multiple closely spaced defibrillation pulses to a heart.

2. The electrical circuit of claim 1 wherein the switch means allows for simultaneous charging from the low power output primary defibrillator battery to both the high power output intermediate power intensifying battery and the main energy delivery capacitor.

3. The electrical circuit of claim 1 in which the primary battery has a maximum current output of about 3 amps.

4. The electrical circuit of claim 1 in which the switch means selectively recharges the intermediate power intensifying battery from the primary defibrillator battery.

5. The electrical circuit of claim 4 in which the intermediate power intensifying battery has a maximum current output within a range of between 10 amps and 30 amps.

6. The electrical circuit of claim 1 in which the switch means selectively switches between the primary defibrillation battery and the intensifying battery so that sufficient energy is provided to the energy delivery capacitor and the energy delivery capacitor is charged in a time interval which is within a range of greater than 10 milliseconds and less than 1 second between pulses.

7. The electrical circuit of claim 1 in which the switch means provides the main energy delivery capacitor a charging a rate of between 10 joules per second and 100 joules per second.

8. The electrical circuit of claim 1 further comprising control means for switchably inverting the delivery capacitor polarity during the delivery of the first and subsequent pulses so that the pulses are bi-phasic.

9. A main energy delivery electrical circuit for use in an implantable cardioverter defibrillator, comprising:
   a) a low power output primary defibrillator battery;
   b) a high power output intermediate power intensifying battery;
   c) a main energy delivery capacitor for discharging, in a first pulse, an electrical charge derived from the primary defibrillator battery and for discharging certain subsequent pulses of electrical charge derived from the intermediate power intensifying battery; and
   d) sub-circuit means for allowing simultaneous charging from the low power output primary defibrillator battery to both the high power output intermediate power intensifying battery and the main energy delivery capacitor.

10. The electrical circuit of claim 9 in which the sub-circuit means comprises switch means for permitting the intermediate power intensifying battery to rapidly charge the main energy delivery capacitor.

11. The electrical circuit of claim 9 wherein the sub-circuit means provides for simultaneous charging for the first electrical pulse from the low power output primary defibrillator battery and the high power output intermediate power intensifying battery.

12. The electrical circuit of claim 9 in which the primary defibrillator battery has a maximum current output of about 3 amps.

13. The electrical circuit of claim 9 in which the intermediate power intensifying battery has a maximum current output within a range of between 10 amps and 30 amps.

14. The electrical circuit of claim 9 in which the sub-circuit means includes means for repeatably charging the delivery capacitor in a time interval which is less than 5 seconds between pulses.

15. The electrical circuit of claim 14 in which the time interval is within a range of greater than 10 milliseconds and less than 1 second between pulses.

16. The electrical circuit of claim 9 in which the sub-circuit means provides the main energy delivery capacitor a charging rate of between 10 joules per second and 100 joules per second.

17. The electrical circuit of claim 9 further comprising current reversal means for inverting a delivery capacitor polarity during a delivery of the first and subsequent pulses so that the pulses are biphasic.

18. A rapid pulse power system electrical circuit for use with an implantable cardioverter defibrillator to rapidly transition from a widely spaced defibrillation pulse sequence to a closely spaced defibrillation pulse sequence, comprising:

a main energy delivery capacitor for charging and then discharging electrical energy as a defibrillation pulse;
a low power output primary defibrillator battery;
a high power output intermediate power intensifying battery;
switch means for selectively permitting the primary defibrillator battery and the intermediate power intensifying battery to rapidly charge the main energy delivery capacitor;
first control means for responding to a remote signal and selectively discharging the main energy delivery capacitor; and
second control means for controlling the switch means and the main energy delivery capacitor for charging a first electrical energy pulse and for charging certain subsequent pulses of electrical charge derived from the intermediate power intensifying battery so that the electrical circuit permits the implantable cardioverter defibrillator device to deliver multiple closely spaced defibrillation pulses to a heart at any time interval following an initial defibrillation attempt by the first electrical energy pulse.

19. The electrical circuit of claim 18 in which the primary battery has a maximum current output of about 3 amps.

20. The electrical circuit of claim 18 in which the intermediate power intensifying battery has a maximum current output within a range of between 10 amps and 30 amps.

21. The electrical circuit of claim 18 in which the second control means can selectively switch between the primary defibrillation battery and the intensifying battery so that sufficient energy is provided to the delivery capacitor such that the delivery capacitor is repeatably able to charge and then discharge in a time interval which is less than 5 seconds between pulses.

22. The electrical circuit of claim 21 in which the time interval is within a range of greater than 10 milliseconds and less than 1 second.

23. The electrical circuit of claim 18 in which the second control means provides the main energy delivery capacitor a charging rate of between 10 joules per second and 100 joules per second.

24. The electrical circuit of claim 18 further comprising electrical discharge reversal means for switchably inverting a delivery capacitor polarity during a delivery of the electrical energy pulses so that the pulses are biphasic.

25. A method for configuring an implantable cardioverter defibrillator main energy delivery electrical circuit for delivery of multiple closely spaced defibrillation pulses to a heart comprising the steps of:
   a) providing a low power output primary defibrillator battery;
   b) providing a high power output intermediate power intensifying battery;
   c) providing a switch mechanism for permitting the intermediate power intensifying battery to be selectively rechargeable from the primary defibrillator battery;
   d) providing a main energy delivery capacitor;
   e) charging the main energy delivery capacitor with electrical energy derived from the primary defibrillator battery as a first pulse of electrical charge;
   f) discharging the first pulse of electrical charge as a defibrillation pulse;

g) subsequently recharging the main energy delivery capacitor one or more times with electrical energy as subsequent pulses of electrical charge derived from the intermediate power intensifying battery; and h) discharging the subsequent pulses of electrical charge so that the electrical circuit permits the implantable cardioverter defibrillator device to deliver multiple closely spaced defibrillation pulses to a heart.

26. The method of claim 25 further comprising the step of simultaneously charging both the high power output intermediate power intensifying battery and the main energy delivery capacitor using the low power output primary defibrillator battery.

27. A method of configuring an implantable cardioverter defibrillator electrical circuit as a rapid pulse power system to enable rapid transition from a widely spaced defibrillation pulse sequence to a closely spaced defibrillation pulse sequence, comprising the steps of:

sensing ventricular arrhythmia and providing a remote signal upon detection of a ventricular arrhythmia:

providing a low power output primary defibrillator battery;

providing a high power output intermediate power intensifying battery;

providing a main energy delivery capacitor:

providing switch means for selectively permitting the primary defibrillator battery and the intermediate power intensifying battery to rapidly charge the main energy delivery capacitor; and responding to the remote signal and selectively discharging the main energy delivery capacitor so that the main energy delivery capacitor discharges, in a first pulse, an electrical charge and, in certain subsequent multiple closely spaced defibrillation pulses, discharges electrical charge derived from the intermediate power intensifying battery, the pulses being deliverable to a heart at any time interval following an initial defibrillation attempt.

* * * * *